(12) United States Patent
McDonald et al.

(10) Patent No.: US 7,278,236 B2
(45) Date of Patent: Oct. 9, 2007

(54) PLANT ROOT CHARACTERIZATION SYSTEM

(75) Inventors: Daniel W. McDonald, Knoxville, TN (US); Ronald B. Michaels, Seymour, TN (US)

(73) Assignee: Phenotype Screening Corporation, Seymour, TN (US)

( * ) Notice: Subject to any disclaimer, the term of this patent is extended or adjusted under 35 U.S.C. 154(b) by 81 days.

(21) Appl. No.: 11/083,128

(22) Filed: Mar. 17, 2005

(65) Prior Publication Data

US 2006/0207172 A1 Sep. 21, 2006

(51) Int. Cl.
*A01C 1/00* (2006.01)
(52) U.S. Cl. .................................................. 47/1.01 R
(58) Field of Classification Search ............ 47/DIG. 8, 47/1.01 R, 58.1
See application file for complete search history.

(56) References Cited

OTHER PUBLICATIONS

D.A. Heeraman et al., Three Dimensional Imaging of Plant Roots in Situ with X-ray Computed Tomography; ☐☐Hydrology, Department of Land, Air and Water Resources (LAWR), University of California, Davis;☐☐Plant and Soil 189; pp. 167-179; 1997.*
Dr. P. Jenneson, Radiation Imaging of Nutrient Uptake in Biological Root Systems Using Cone-Beam X-ray Micro-CT;☐☐University of Reading, Department of Soil Science, 1999.*

Pierret et al., Simultaneous X-ray Imaging of Plant Root and Water Uptake in Thin Slab Systems; Plant and Soil Journal, Netherlands, vol. 255, No. 1/Aug. 2003; pp. 361-373.*

* cited by examiner

*Primary Examiner*—Francis T. Palo
(74) *Attorney, Agent, or Firm*—Luedeka, Neely & Graham, P.C.

(57) ABSTRACT

An apparatus and method for nondestructively acquiring images of a plant root system is described. The apparatus includes a substrate for supporting the plant root system, a container for holding the substrate, an x-ray radiation source for generating x-ray radiation and directing the radiation to pass through the plant root system, and an x-ray image capture system for receiving the x-ray radiation having passed through the plant root system and for generating an image of the plant root system based on the radiation. The x-ray radiation source generates x-ray radiation having an energy level in the range of about 8 keV to about 20 keV. In this energy range, the attenuation of the x-ray radiation due to air is minimized and the contrast between the root system and the container and substrate is sufficiently high to provide a resolvable image. The substrate and container are preferably formed of materials having a low mass density, such as less than about 3 pounds per cubic foot, and a low x-ray mass attenuation coefficient. The low density materials of the substrate and the container introduce comparatively low attenuation of the x-ray radiation when compared to the attenuation introduced by the roots, thereby enhancing the visibility of the root system in the image.

20 Claims, 5 Drawing Sheets

PLANT ROOT CHARACTERIZATION SYSTEM

FIELD

This invention relates to the field of imaging systems. More particularly, this invention relates to generating x-ray images of plant roots while the plant is in a growth substrate and container.

BACKGROUND

One goal of functional genomic research is to accelerate the improvement of plants used for food, pharmaceuticals, ornamentals, biofuels, biopower, biochemicals, carbon sequestration, and materials. Many functional genomic research programs focus on how changes to individual genes affect a plant's root system. Such programs generally apply high-throughput, large-scale experimental methodologies combined with statistical and computational analysis of the results. It is not unusual for tens of thousands of plant specimens to be studied in order to deduce the function of a single gene in the plant. In these types of research programs, the ability to analyze plant root structure and function in a timely, cost efficient manner is vital.

High-throughput cost efficient root imaging is also needed in root growth research programs and in the screening of cultivars developed through traditional breeding programs.

A destructive method of studying plant roots consists of taking the plant and its surrounding soil out of the container in which it was growing, washing the soil from the plant roots, and imaging the roots using a desktop flatbed scanner.

Another method for imaging plant roots is performed using devices called rhizotrons. These are transparent tubes that are placed in the ground. After plant roots grow around the rhizotron, a visible light camera is placed in the tube for capturing images of the plant roots that are on the external surface of the rhizotron.

Another method uses computed x-ray tomography to acquire several hundred high energy x-ray images of the roots taken at slightly different angles. Special computer algorithms are used to reconstruct an approximate three-dimensional image of the root system. With this method approximate root structure information can be extracted even though the roots are hidden by surrounding soil. The technique requires that the soil be specially processed to be highly homogeneous in both size and composition. The penalty one pays for this capability is the need for many images, thus precluding high throughput performance and providing lower resolution.

Yet another method is to grow plants in custom growth chambers i.e., between two transparent sheets with transparent glass beads as a substrate and use traditional visual imaging technology.

None of these prior methods provide a nondestructive high-throughput technology that supports large-scale plant root characterization studies. Thus, there is a need for a high resolution, high throughput, nondestructive, noninvasive root characterization system.

SUMMARY

The above and other needs are met by a plant root characterization system that generates digital x-ray images of plant roots using low-energy x-ray exposure while the plant remains undisturbed in a growth substrate in a container. Root structural features are extracted from the resulting digital images in order to characterize the root system for phenotype screening. One preferred embodiment of the system includes a plant container, a plant growth substrate, an x-ray generator, a digital x-ray image capture system and digital image processing software. Some embodiments of the invention also include a specimen presentation stage, a nutrient solution removal system and a plant substrate rehydration system.

The plant container holds the plant substrate which supports the root structure of the plant specimen, and provides for ease of handling of individual plant specimens. The container constricts root growth to a known volume and restricts light flux to the plant roots. The container allows for implementation of individual water protocols and nutrient protocols for each plant. The container also forms a plenum for nutrient solution removal. Preferably, the container has uniformly thin flat parallel sidewalls made from low x-ray attenuation materials for improved x-ray imaging.

The plant growth substrate supports the plant root system in the container by providing a superstructure for root growth and plant physical stability. The substrate supports plant seed germination, allows for moisture and nutrient distribution and retention to support plant growth, and provides for proper exposure of the root system to air while allowing for nutrient solution evacuation from inside the container. The substrate preferably has a uniform cross-section and is made of low x-ray attenuation material for improved x-ray imaging. In the preferred embodiment, the substrate is biologically benign, so that all nutrients, symbiotic organisms and parasites are externally provided.

The plant germination and growth protocols provide optimal growth conditions for seed germination and plant growth. Generally, the optimum depth of seeds for sprouting, light levels and nutrient solution application protocols are related to the properties of the plant growth substrate and the specific species of plant.

Plant nutrient solution in the substrate attenuates x-ray radiation, thereby degrading the quality of x-ray images of plant roots growing in the substrate. In the preferred embodiment of the invention, the nutrient solution removal system solves this problem by evacuating plant nutrient solution from the x-ray image area of the growth substrate. The plant nutrient solution removal system removes sufficient nutrient solution from the substrate to allow x-ray imaging of the plant root system without damage to the root system due to dehydration or root deformation. The plant nutrient solution removal system preferably includes one or more sensors that monitor moisture content in the plant growth substrate and indicate when sufficient plant nutrient solution has been removed.

The plant substrate rehydration system is used to replace plant nutrient solution after x-ray imaging. Typically, this is done immediately after the imaging process in order to prevent or minimize damage to the plant root system due to dehydration.

The x-ray generator generates x-ray radiation in an optimum energy range for plant root imaging. The choice of x-ray generator and the settings of the x-ray generator power supply determine the x-ray energy level and the x-ray flux available. The contrast and resolution of the x-ray image is determined at least in part by the x-ray generator.

The specimen presentation stage controls the positioning of the specimen during the imaging process, where the placement of the specimen determines what is imaged by the x-ray system. In the preferred embodiment, the specimen presentation stage selectively positions the plant container between the x-ray generator and the x-ray imaging system.

Preferably, the presentation stage provides for raising, lowering and rotating the plant specimen. The specimen presentation stage provides for positioning the container to multiple positions to capture multiple x-ray images of the plant specimen. The specimen presentation stage also provides for precisely repositioning at a later time to a position at which a previous image was captured. In a preferred embodiment, the specimen presentation stage also determines the x-ray image magnification factor. With these features, the specimen presentation stage allows the system to accommodate a wide variety of plant specimens of varying sizes and growth stages.

The digital x-ray image capture system converts the x-ray image flux into a digital image data file for storage and analysis. This system at least partially determines the x-ray image contrast and resolution and the overall quality of the conversion of the x-ray flux at the sensor to the final data values in the image data file. The conversion of x-ray image flux to digital data allows for digital data storage, retrieval, manipulation and analysis of the image data.

The digital image processing software enhances the x-ray image to provide useful plant root characterization information from the x-ray image data files.

In one preferred embodiment, the invention provides an apparatus for nondestructively acquiring images of a plant root system. In this preferred embodiment, the apparatus includes a substrate for supporting the plant root system, a container for holding the substrate, a radiation source for generating radiation and directing the radiation to pass through the plant root system, and an image capture system for receiving the radiation having passed through the plant root system and for generating an image of the plant root system based on the radiation. The substrate of this embodiment comprises a growth medium having a low radiation attenuation coefficient. The container of this embodiment is also formed of a material having a low radiation attenuation coefficient. Because the low radiation attenuation coefficient materials of the substrate and the container offer minimal attenuation of the radiation passing there through, the visibility of the root system in the image is enhanced.

In another preferred embodiment, the invention provides an apparatus for nondestructively acquiring images of a plant root system. In this embodiment, the apparatus includes a substrate for supporting the plant root system, a container for holding the substrate, an x-ray radiation source for generating x-ray radiation and directing the radiation to pass through the plant root system, and an x-ray image capture system for receiving the x-ray radiation having passed through the plant root system and for generating an image of the plant root system based on the radiation. The x-ray radiation source of this embodiment generates x-ray radiation having an energy level in the range of about 8 keV to about 20 keV. In this energy range, the attenuation of the x-ray radiation due to air is minimized and the contrast between the root system and the container and substrate is sufficiently high to provide a resolvable image.

In another aspect, the invention provides a method for nondestructively acquiring images of a plant root system. The method includes steps of supporting the plant root system in a substrate comprising a growth medium having a linear x-ray attenuation coefficient of no greater than about 0.3 per centimeter at an x-ray energy level of 10 keV, holding the substrate within a container formed of a material having a linear x-ray attenuation coefficient of no greater than about 0.1 per centimeter at an x-ray energy level of 10 keV, generating x-ray radiation having an energy level in the range of about 8 keV to about 20 keV and directing the x-ray radiation to pass through the plant root system, and capturing one or more x-ray images of the plant root system based on the x-ray radiation having passed through the plant root system.

In preferred embodiments, the method also includes steps of removing moisture from the substrate prior to directing the x-ray radiation to pass through the plant root system, and restoring moisture to the substrate after capturing one or more x-ray images of the plant root system. The method may also include the step of selectively positioning the container in relation to the x-ray radiation source and the x-ray image capture system to capture one or more images of a selected portion of the plant root system.

BRIEF DESCRIPTION OF THE DRAWINGS

Further advantages of the invention are apparent by reference to the detailed description in conjunction with the figures, wherein elements are not to scale so as to more clearly show the details, wherein like reference numbers indicate like elements throughout the several views, and wherein.

DETAILED DESCRIPTION

Figure 1:
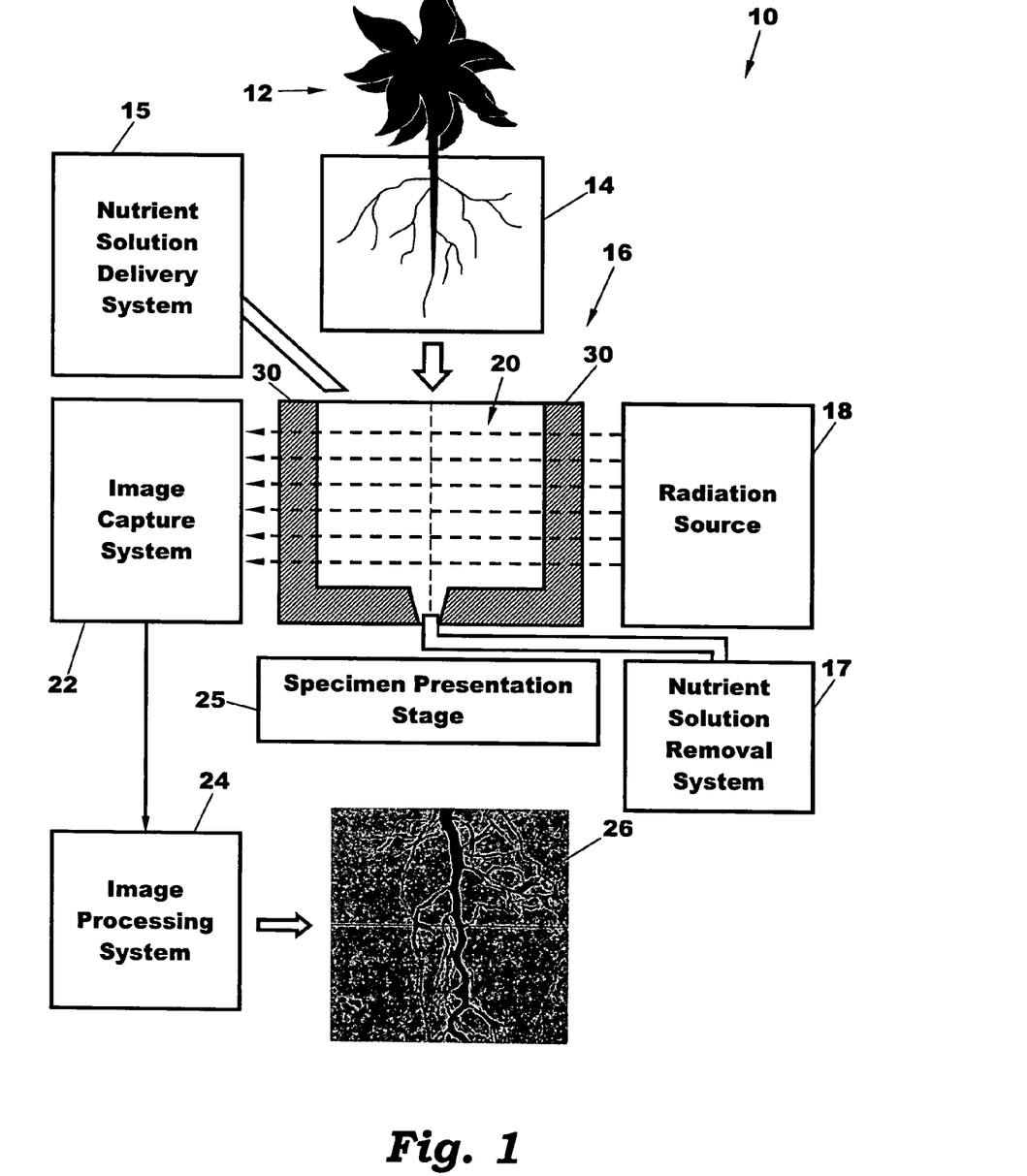
FIG. 1 depicts a plant root characterization system according to a preferred embodiment of the invention.

FIG. 1 depicts a preferred embodiment of a plant root characterization system 10 for characterizing the roots of a plant 12. In this preferred embodiment, the system 10 includes a plant growth substrate 14, a nutrient solution delivery system 15, a plant container 16, a nutrient solution removal system 17, a radiation source 18, an image capture system 22, an image processing system 24 and a plant specimen presentation stage 25. The system 10 operates by passing radiation, such as x-rays, through the plant container 16 containing the substrate 14 in which the root system of the plant 12 is growing. The image capture system 22 captures the radiation passing through the root system to form an image of the root system. The image processing system 24 operates on the captured image 26 to enhance its visual quality and extract useful characteristics of its structure and growth.

The plant growth substrate 14 is the medium which supports the roots of the plant 12. Preferably, the substrate 14 is formed from a material that supports seed germination and normal plant and root development and which has low plant nutrient solution retention and easy rehydration.

The preferred substrate material also has low mass density and a low x-ray mass attenuation coefficient. Preferably, the mass density of the substrate material is no greater than about 0.06 g/cm$^3$, and the x-ray mass attenuation coefficient ($\mu/\rho$) is no greater than about 4.5 cm$^2$/g at a photon energy of about 10 keV. Based on these values of mass density and the x-ray mass attenuation coefficient, the material of a preferred embodiment of the substrate has a linear x-ray attenuation coefficient of about $$0.06 \text{ gm/cm}^3 \times 4.5 \text{ cm}^2/\text{g} = 0.27 \text{ cm}^{-1} \text{ at an x-ray energy level of 10 keV,}$$

and preferably no greater than about 0.3 cm$^1$. Materials meeting these requirements include urethane foam and polyester fiber batting or mats, such as are used for pillow stuffing and quilt batting. In one preferred embodiment, the growth substrate material is Medius™ growing medium manufactured by CP Medius. However, it will be appreciated that other materials could also be used as the growth substrate 14.

Figures 2A, 2B:
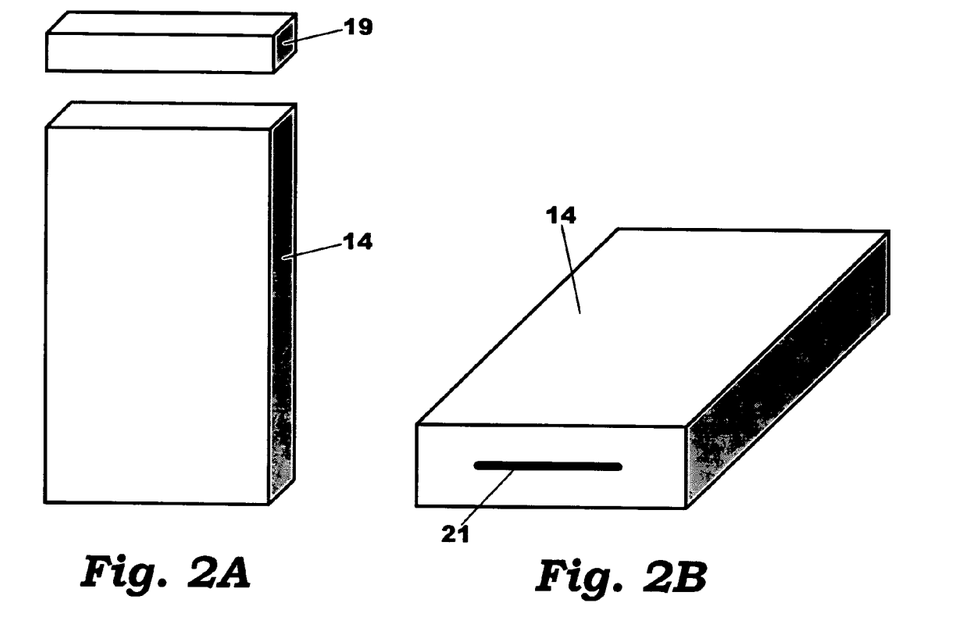
FIGS. 2A-2D depict plant growth substrates according to preferred embodiments of the invention.
Figure 2C:
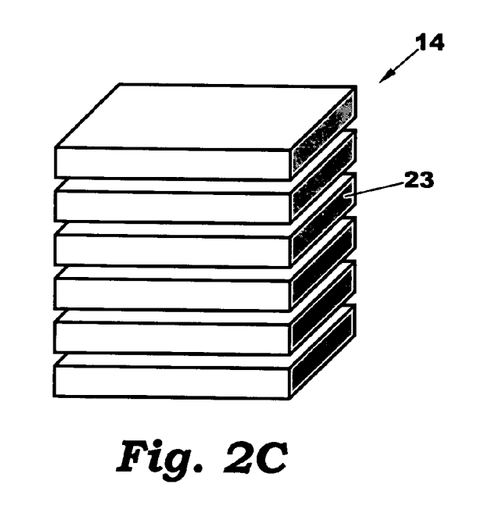
Figure 2D:
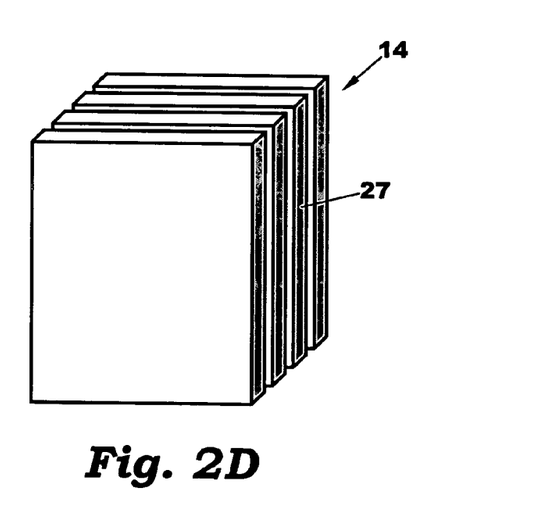

In a preferred embodiment depicted in FIGS. 2A and 2B, the substrate 14 is a rectangular plug having dimensions of about 50×30×200 mm. In other embodiments, the substrate 14 comprises horizontally stacked rectangular sheets 23 as shown in FIG. 2C, or vertically stacked rectangular sheets 27 as depicted in FIG. 2D. In yet other embodiments, the substrate 14 is cylindrical. Whatever the shape and configuration of the substrate 14, it is preferably compatible for ease of insertion into and removal from a cavity 20 within the container 16.

As shown in FIG. 2A, preferred embodiments include a germination cap 19. The germination cap 19 comprises a thin slice of substrate material that covers some types of seeds during germination. After germination the cap 19 is removed. For other types of seeds, no covering is needed. Still other types of seeds require that they be "planted" some distance below the surface of the substrate 14. To accommodate these types of seeds, the embodiment shown in FIG. 2B includes a slit 21 in the top of the substrate 14 into which the seeds are inserted.

The plant container 16 encloses and supports the substrate 14. The container 16 is preferably formed from a material that is homogenous and relatively impermeable to moisture and which has low mass density and low x-ray attenuation. Preferably, the mass density of the container material is no greater than about 0.025 gm/cm$^3$ and the x-ray mass attenuation coefficient ($\mu/\rho$) is no greater than about 2.219 cm$^2$/g at a photon energy of about 10 keV. Based on these values of mass density and the x-ray mass attenuation coefficient, the material of the preferred embodiment of the container has a linear x-ray attenuation coefficient of about $$0.025 \text{ g/cm}^3 \times 2.219 \text{ cm}^2/\text{g} = 0.055 \text{ cm}^{-1} \text{ at an x-ray energy level of 10 keV,}$$

and preferably no greater than about 0.1 cm$^{-1}$. One material meeting these requirements is expanded polystyrene (EPS) foam, from which the container of the preferred embodiment of the invention is formed. However, it will be appreciated that other materials could also be used for the container 16.

Figure 3:
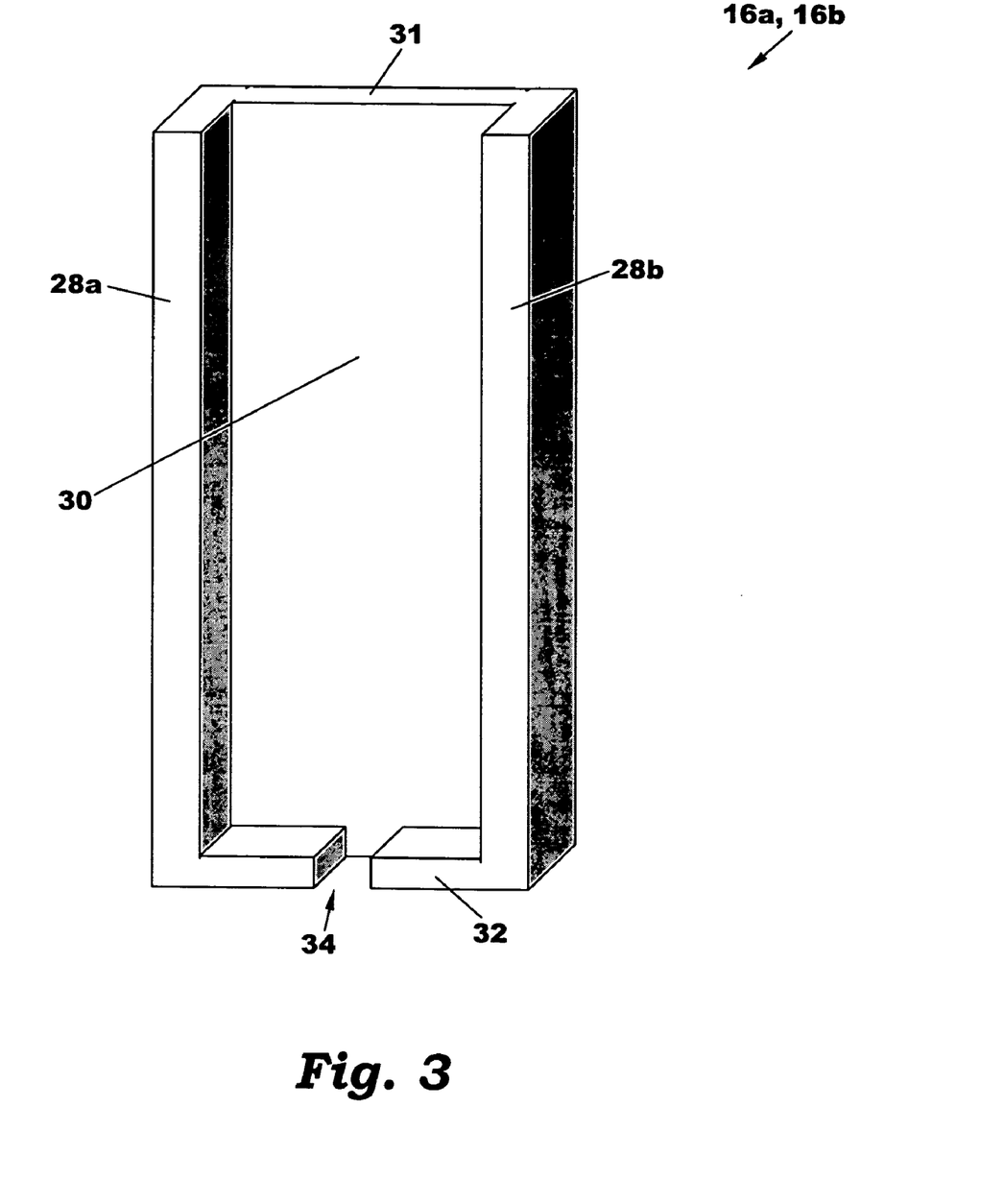
FIG. 3 depicts a portion of a plant container according to a preferred embodiment of the invention.
Figure 4A:
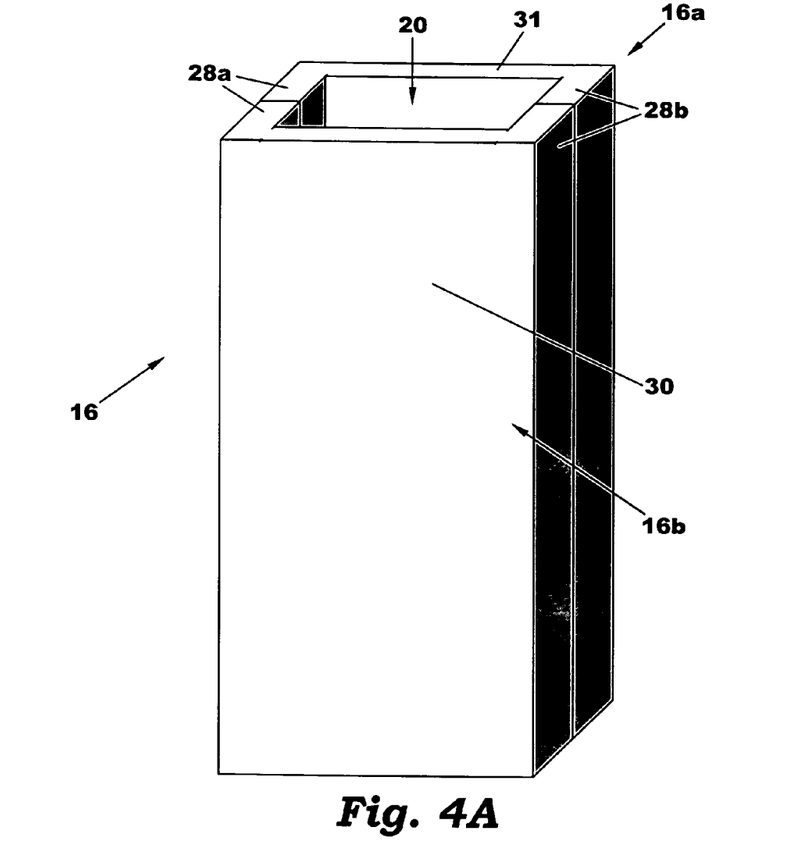
FIGS. 4A-4C depict a plant container according to a preferred embodiment of the invention.
Figure 4B:
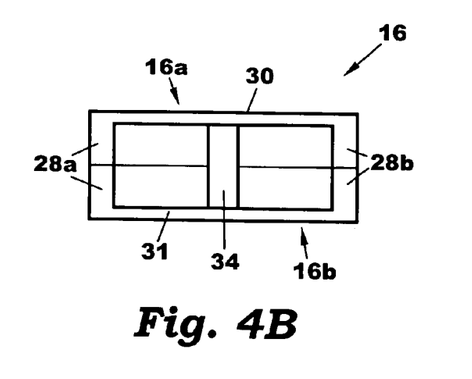
Figure 4C:
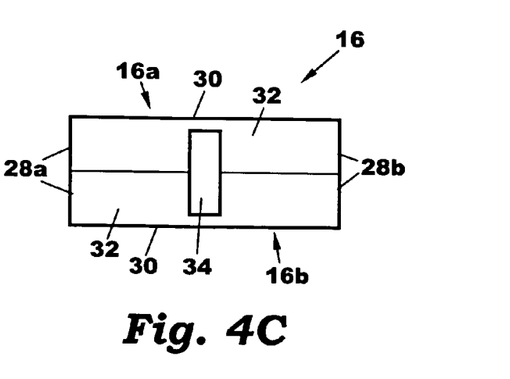

As shown in FIGS. 4A-4C, the container 16 is preferably formed by joining together two identical container halves 16a-16b. The container halves 16a-16b may be joined using an adhesive, by a mechanical clamping structure, or other method. A preferred embodiment of one container half 16a-16b is depicted in FIG. 3. This embodiment has a substantially flat sidewall 30 with uniform cross section and homogeneous composition which minimizes distortion of the imaging radiation as it passes through the sidewall 30. Preferably, the thickness of the sidewall 30 is no more than about 4 mm so as to minimize attenuation to radiation passing through the sidewall 30. In this embodiment, the container halves 16a-16b are joined together at the outer surfaces of the end walls 28a-28b and the bottom wall 32. The bottom wall 32 preferably includes a drain port 34 for draining excess plant nutrient solution. The top 31 of the container 16 is of an open design to allow for easy addition of plant nutrient solution and to maximize the air flow entering the top of the substrate 14 when nutrient solution is evacuated using the nutrient solution removal system applied to the drain port 34.

In a preferred embodiment, the width of the container 16 corresponds to the detection width of the image capture system 22. The height of the container 16 is preferably chosen to match the needs of the specific plant under investigation.

As noted above, it is preferred that the side walls 30 of the container 16 be flat to minimize distortion of the x-ray image passing through the sidewalls 30. However, it should be appreciated that the sidewalls 30 of the container 16 could have other shapes, such as conical or cylindrical. In embodiments of the container 16 having curved sidewalls or sidewalls having nonuniform thickness, additional image processing steps may be needed to compensate for differences in object thickness in different parts of the image.

In another embodiment, the container 16 may be produced as one piece. In a one piece embodiment, it is preferable that the container be tapered to ease the insertion and removal of the substrate 14.

In an alternative embodiment of the invention, the plant container 16 and the growth substrate 14 are combined in a single integral structure by forming the substrate 14 using a polymer molding process that forms a skin on the surface of the substrate 14. In this embodiment, the skin formed in the molding process comprises the container 16.

In yet another embodiment, the plant container 16 is formed of a relatively thin polymer film. This embodiment includes a mechanical frame or other support structure to support the container 16. The growth substrate 14 may provide this structural support if the growth substrate material is sufficiently rigid.

In preferred embodiments of the invention, the radiation source 18 is an x-ray generator. Unlike prior imaging systems using x-ray generators operating at about 50 kiloelectron Volts (keV), the x-ray generator 18 of the preferred embodiment operates in a much lower energy range of about 8-20 keV. According to the invention, the x-ray photon energy level provided by the x-ray generator 18 is high enough to penetrate the plant root system, container and substrate, but low enough to provide sufficient contrast for a digital x-ray camera to generate a high contrast image. Above about 20 keV, the mass attenuation curve for hydrocarbons begins to flatten out. Operation in the area above about 20 keV results in a lower contrast between high density regions (plant roots) and low density regions (substrate and container). Below about 8 keV, the attenuation of x-ray radiation due to the air becomes significant. At energy levels this low, the sensitivity of a digital x-ray camera may not be sufficient to provide a resolvable image. In the 8-20 keV range, the attenuation of the x-ray radiation due to air is less of a factor, and the contrast between roots and container and substrate is sufficiently high to provide a resolvable image.

Another advantage of using relatively low energy x-ray radiation is the minimization of x-ray exposure to the plants under study. Generally, higher energy x-rays expose the plants to more damaging ionizing radiation.

To enhance the resolution of the x-ray image, the spot size generated by the x-ray generator 18 is nominally about 35 microns. One x-ray generator 18 having a desired combination of low cost, small spot size and low energy is the Oxford Instruments Apogee tube. Other generators having smaller spot size are commercially available.

In the preferred embodiment of the invention, the radiation image capture system 22 comprises a two-dimensional digital x-ray camera, such as the ShadowCam™ by Radicon Imaging Corporation. In one embodiment, the camera 22 has a light opaque cover, made of graphite, over a scintillator material that converts x-rays to visible light.

Preferably, the image capture system 22 captures one image at a time of all or a portion of a root system for characterization of that portion. Multiple images may be captured and used to form a tomographic reconstruction or photomontage.

In an alternative embodiment, an x-ray line scan camera can be used to raster scan across the container 16 to build a two-dimensional image of the root system. Although a line scan camera requires a longer time to capture a complete image, it provides a perpendicular view of the root system along the axis of motion. The size of the image in the direction of motion is limited only by the relative motion of the container 16 with respect to the source 18 and the image capture system 22.

The image processing system 24 receives the image from the image capture system 22 and processes the image to enhance the contrast between the roots and the surrounding substrate 14 and container 16. The preferred embodiment of the image processing system includes software that performs a density computation process based at least in part on a comparison to the localized density of a reference material. The density calibration process generally involves the creation of nonlinear calibration curves unique to each pixel of the camera.

The specimen presentation stage 25 preferably comprises a vertically moving stage that provides for positioning the container 16 in multiple positions for capturing multiple x-ray images of the root system. The multiple images may be tiled together into a photomontage to cover an area greater than could be covered in a single image. The specimen presentation stage 25 also preferably includes a rotary stage that can be used to rotate the container 16 around a vertical axis. The rotary stage provides for positioning the container 16 at two slightly different angles at which two images may be captured. Using the two images captured at two different angles, the image processing system 24 can prepare stereo images of the plant root system. Using multiple images captured at different angles, the image processing system can perform a tomographic reconstruction of the root system.

In an alternative embodiment, the specimen presentation stage 25 comprises a horizontally moving stage combined with a vertically moving stage to provide for capturing photomontage images of containers having a width too great to be covered using a single vertical column of images. This approach also allows for multiple plant specimens to be imaged side by side allowing for increased system throughput. The horizontal and vertical stages can also be combined with a rotary stage to provide for 3-axis motion control on a single presentation stage 25.

Generally, different types of plants have different germination requirements and growth rates. As discussed above, to accommodate the study of different types of plant specimens, the invention can incorporate various substrate materials and various container shapes and sizes. The preferred embodiment of the presentation stage 25 provides the required flexibility to hold and manipulate containers of various shapes and sizes.

In the preferred embodiment, the presentation stage 25 is designed to move the container 16 relative to the source 18 and the image capture system 22 while the source 18 and the image capture system 22 remain stationary. In an alternative embodiment, the source 18 and the image capture system 22 move relative to the container 16 while the container 16 remains stationary. Alternatively, the source 18, image capture system 22 and container 16 all move.

In embodiments of the invention designed to capture a single image per specimen, the specimen presentation stage 25 comprises a stationary fixture that positions each specimen container 16 in the same position relative to the source 18 and the image capture system 22.

Generally, different plants have different germination requirements and different water and nutrient requirements. Also different substrate materials have different moisture distribution and moisture retention properties. In order to assure germination and robust plant growth, specific protocols or regimens are employed based upon the specifics of the plant, the substrate and the timing of the acquisition of the x-ray image. Generally the requirements for germination are different from the requirements for sustaining robust plant growth. In addition to water and nutrient control, the temperature, humidity and light levels applied to the plant environment are also specified and controlled.

As shown in the preferred embodiment depicted in FIG. 1, the nutrient solution delivery system 15 is employed to maintain the proper water/nutrient mix within the substrate 14 to support germination and later to support robust plant growth. In general, the water and nutrients are premixed for the specific plant needs. The delivery system 15 preferably comprises a timer, pump and tubing that delivers the nutrient solution at the proper time intervals to the top of the container 16. The time intervals and durations of nutrient delivery depend on the specifics of the plant specimen and the substrate material.

In the operating x-ray energy range of the invention, water significantly attenuates x-ray energy. As shown in FIG. 1, the preferred embodiment of the root characterization system 10 includes the nutrient solution removal system 17 for removing sufficient water and nutrient solution from the substrate 14 to provide clear x-ray images without damaging fine root structure. The nutrient solution removal system 17 preferably comprises a vacuum system connected to the drain port 34. The amount of negative pressure applied and the duration of the application is a function of the plant/substrate combination of interest. During operation of the nutrient solution removal system 17, care is taken to assure that fragile components of the plant such as root hairs are not damaged by the vacuum settings employed.

For some plant/substrate combinations the nutrient solution drains fairly quickly from the substrate. In these situations, x-ray image acquisition can occur without the need for the nutrient solution removal system 17. With other plant/substrate combinations, the nutrient solution can only be adequately removed by active means, such as provided by the nutrient solution removal system 17.

In the preferred embodiment, the moisture content of the substrate 14 is monitored by weighing the plant/substrate/container one or more times during the moisture removal process. In an alternative embodiment, the moisture removal system 40 includes a capacitive sensor for monitoring moisture content within the substrate 14. As moisture content changes, the potential difference between capacitor plates of the sensor changes. This change in potential difference is measured and related to a moisture content value.

In yet another alternative embodiment, the image capture system 22 can be used to capture one or more images of the moisture distribution within the container 14 before and during the moisture evacuation process. The resulting images indicate when sufficient nutrient solution has been removed to provide quality images of the root system. The resulting images could also provide valuable data about moisture distribution within the substrate 14. The images could also provide an indication of the water retention capabilities of root systems.

Preferably, the nutrient solution delivery system 15 is used to reintroduce nutrients and water to the substrate 14 after completion of the image capture process. In some embodiments, the x-ray imaging components are remote from the nutrient solution delivery system 15. In other embodiments the x-ray imaging components and the nutrient solution delivery system 15 are collocated. Thus, it should be appreciated that the invention is not limited to any particular spatial relationship between the x-ray imaging components and the nutrient solution delivery system 15.

In one embodiment, the invention comprises an automated, robotic plant handling system. In this embodiment, each plant specimen container is identified using some type of marker, such as a bar code. The container is automatically moved from a holding station to a nutrient solution removal station where nutrient solution removal is automatically monitored. After nutrient solution removal, the automated system moves the plant container to an imaging station, captures one or more images, processes the image data, saves the data in data files, moves the container to a rehydration station and moves the container to an output storage tray.

Figure 5:
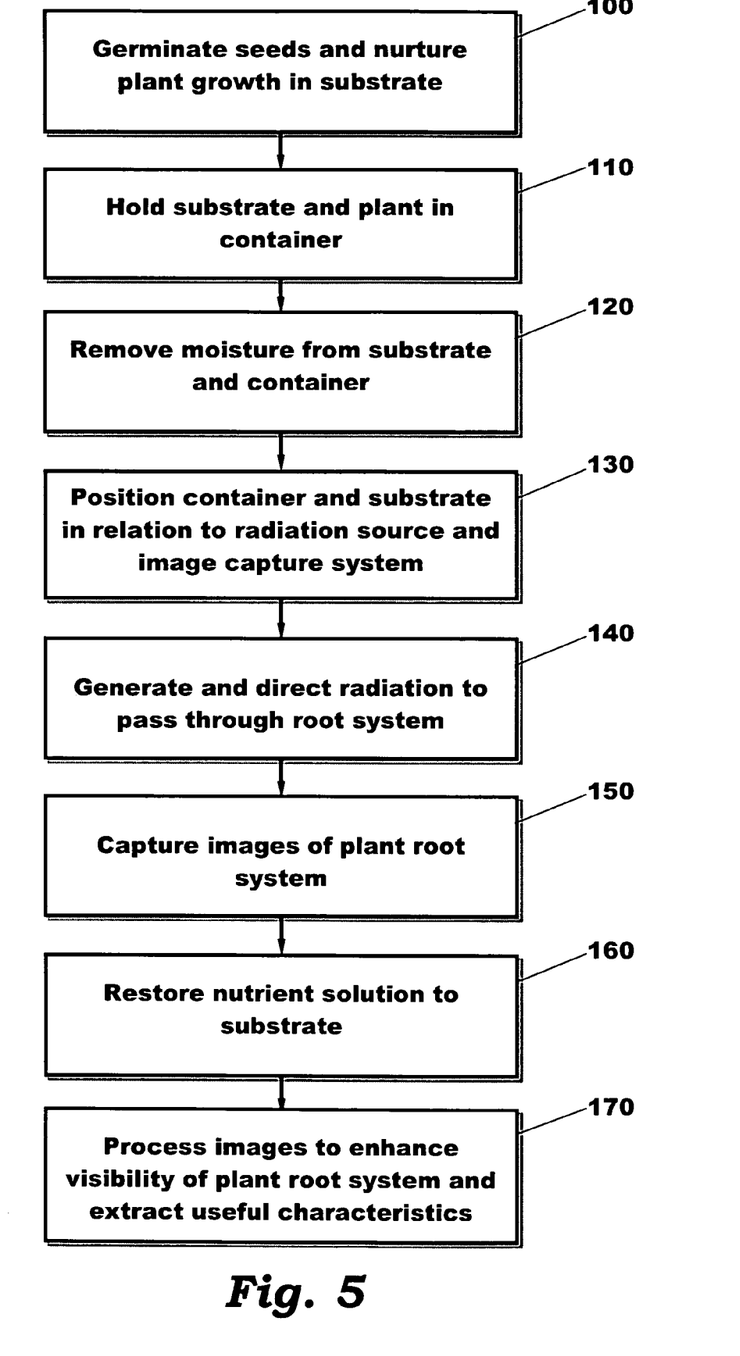
FIG. 5 depicts a method for capturing images of a root system according to a preferred embodiment of the invention.

With reference to FIG. 5, the apparatus described above may be used to perform a method for nondestructively acquiring images of a plant root system. In a preferred embodiment, the method includes steps of germinating seeds and nurturing plant growth in a substrate comprising a low x-ray attenuation substrate (step 100), holding the substrate and plant within a container formed of a low x-ray attenuation substrate material (step 110), removing moisture from the substrate and container (step 120) and selectively positioning the container and substrate in relation to an x-ray radiation source and an x-ray image capture system (step 130). The method also includes steps of generating x-ray radiation having an energy level in the range of about 8 keV to about 20 keV and directing the x-ray radiation to pass through the plant root system (step 140), and capturing one or more x-ray images of the plant root system based on the x-ray radiation having passed through the plant root system (step 150). After capturing the x-ray images, nutrient solution is restored to the substrate (step 160). In preferred embodiments, the method also includes the step of enhancing visual qualities of the x-ray images captured by the x-ray image capture system (step 170), such as by using image processing software.

The foregoing description of preferred embodiments for this invention have been presented for purposes of illustration and description. They are not intended to be exhaustive or to limit the invention to the precise form disclosed. Obvious modifications or variations are possible in light of the above teachings. The embodiments are chosen and described in an effort to provide the best illustrations of the principles of the invention and its practical application, and to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

What is claimed is:

1. An apparatus for nondestructively acquiring images of a plant root system comprising root material having a first linear radiation attenuation coefficient, the apparatus comprising:
   a substrate for supporting the plant root system, the substrate comprising a growth medium having a second linear radiation attenuation coefficient which is less than about 10 percent of the first linear radiation attenuation coefficient;
   a container for holding the substrate, the container formed of a material having a third linear radiation attenuation coefficient which is less than about 10 percent of the first linear radiation attenuation coefficient;
   a radiation source for generating radiation and directing the radiation to pass through the plant root system; and
   an image capture system for receiving the radiation having passed through the plant root system and for generating an image of the plant root system based on the radiation.

2. The apparatus of claim 1 further comprising a presentation stage for selectively positioning the container in relation to the radiation source and image capture system.

3. The apparatus of claim 1 further comprising an image processing system for enhancing visual qualities of the image generated by the image capture system.

4. The apparatus of claim 1 wherein the substrate comprises polyester fiber batting.

5. The apparatus of claim 1 wherein the substrate comprises a porous foam material.

6. The apparatus of claim 1 wherein the container is formed of expanded polystyrene.

7. The apparatus of claim 1 wherein the container comprises a skin formed on the substrate during a polymer molding process, whereby the container and substrate comprise an integral structure.

8. The apparatus of claim 1 wherein the container comprises a resin film.

9. The apparatus of claim 1 wherein the container comprises:
   a first container portion having a first sidewall, at least a first portion of two end walls and at least a first portion of a bottom wall; and
   a second container portion having at least a second sidewall,
   wherein the first container portion is removably attached to the second container portion.

10. The apparatus of claim 9 wherein the second container portion is substantially identical in structure to the first container portion, the second container portion further comprising at least a second portion of two end walls and at least a second portion of a bottom wall, wherein the second portion of two end walls is removably attached to the first portion of two end walls and the second portion of a bottom wall is removably attached to the first portion of a bottom wall.

11. The apparatus of claim 9 wherein the first portion of a bottom wall of the first container portion includes at least a portion of a drain port.

12. The apparatus of claim 1 wherein the radiation source comprises an x-ray source and the image capture system comprises an x-ray image capture system.

13. The apparatus of claim 12 wherein the x-ray source generates x-ray radiation at an energy level in the range of about 8 keV to about 20 keV.

14. The apparatus of claim 1 further comprising a moisture removal system for removing moisture from the substrate prior to capturing one or more images of the plant root system.

15. The apparatus of claim 1 further comprising a rehydration system for restoring moisture to the substrate after capturing one or more images of the plant root system.

16. An apparatus for nondestructively acquiring images of a plant root system, the apparatus comprising:

a substrate for supporting the plant root system;

a container for holding the substrate;

an x-ray radiation source for generating x-ray radiation having an energy level in the range of about 8 keV to about 20 keV and directing the radiation to pass through the plant root system; and     an x-ray image capture system for receiving the x-ray radiation having passed through the plant root system and for generating an image of the plant root system based on the radiation.

17. A method for nondestructively acquiring images of a plant root system, the method comprising:

(a) supporting the plant root system in a substrate comprising a growth medium having a linear x-ray attenuation coefficient of no greater than about 0.3 per centimeter at an x-ray energy level of about 10 keV;

(b) generating x-ray radiation having an energy level in the range of about 8 keV to about 20 keV and directing the x-ray radiation to pass through the plant root system; and     (c) capturing one or more x-ray images of the plant root system based on the x-ray radiation having passed through the plant root system.

18. The method of claim 17 further comprising:

(d) removing moisture from the substrate prior to directing the x-ray radiation to pass through the plant root system; and     (e) restoring moisture to the substrate after capturing one or more x-ray images of the plant root system.

19. The method of claim 17 further comprising selectively positioning the container in relation to the x-ray radiation source and the x-ray image capture system to capture one or more images of a selected portion of the plant root system.

20. The method of claim 17 further comprising holding the substrate within a container formed of a material having a linear x-ray attenuation coefficient of no greater than about 0.1 per centimeter at an x-ray energy level of about 10 keV.

\* \* \* \* \*